United States Patent
Roh

(10) Patent No.: US 12,336,848 B2
(45) Date of Patent: Jun. 24, 2025

(54) APPARATUS FOR MEASURING DEGREE OF FRAILTY ON BASIS OF ATHLETIC ABILITY PARAMETERS

(71) Applicant: DYPHI INC., Daejeon (KR)

(72) Inventor: Hyun Chul Roh, Daejeon (KR)

(73) Assignee: Dyphi Inc., Daejeon (KR)

( * ) Notice: Subject to any disclaimer, the term of this patent is extended or adjusted under 35 U.S.C. 154(b) by 0 days.

(21) Appl. No.: 18/634,465

(22) Filed: Apr. 12, 2024

(65) Prior Publication Data

US 2024/0341696 A1 Oct. 17, 2024

Related U.S. Application Data

(63) Continuation of application No. 16/979,825, filed as application No. PCT/KR2019/003746 on Mar. 29, 2019, now Pat. No. 11,986,324.

(30) Foreign Application Priority Data

Apr. 4, 2018 (KR) .......................... 10-2018-0039333

(51) Int. Cl.
*A61B 5/00* (2006.01)
*A61B 5/11* (2006.01)
(Continued)

(52) U.S. Cl.
CPC .......... *A61B 5/7275* (2013.01); *A61B 5/1118* (2013.01); *A61B 5/112* (2013.01);
(Continued)

(58) Field of Classification Search
CPC .................................................. A61B 5/7275
(Continued)

(56) References Cited

U.S. PATENT DOCUMENTS

2013/0289449 A1* 10/2013 Stone .................. A61B 5/0013
600/595
2014/0257047 A1* 9/2014 Sillay ...................... H04L 63/10
600/595

(Continued)

FOREIGN PATENT DOCUMENTS

JP 2002-165799 A 6/2002
JP 2015-042241 A 3/2015
(Continued)

OTHER PUBLICATIONS

International Search Report mailed on Jul. 5, 2019, issued in connection with International Application No. PCT/KR2019/003746, filed on Mar. 29, 2019, 4 pages.

(Continued)

*Primary Examiner* — Nadia A Mahmood
(74) *Attorney, Agent, or Firm* — McDonnell Boehnen Hulbert & Berghoff LLP

(57) ABSTRACT

Disclosed herein is a frailty diagnosis apparatus. The frailty diagnosis apparatus includes a physical performance meter and a processor for determining a frailty index of a target person based on physical performance of the target person obtained by the physical performance meter. The physical performance meter includes at least one among a gait speed meter for measuring a gait speed of the target person, a body balance meter for measuring a body balance maintenance time of the target person, and a muscle strength meter for measuring a muscle exercise time.

15 Claims, 7 Drawing Sheets

(51) Int. Cl.
| | |
|---|---|
| *A61B 5/22* | (2006.01) |
| *G16H 10/60* | (2018.01) |
| *G16H 40/67* | (2018.01) |
| *G16H 50/20* | (2018.01) |
| *G16H 50/30* | (2018.01) |
| *G16H 50/70* | (2018.01) |

(52) U.S. Cl.
CPC ............ *A61B 5/224* (2013.01); *A61B 5/4023* (2013.01); *A61B 5/4088* (2013.01); *G16H 10/60* (2018.01); *G16H 40/67* (2018.01); *G16H 50/20* (2018.01); *G16H 50/30* (2018.01); *G16H 50/70* (2018.01); *A61B 2562/0219* (2013.01); *A61B 2562/0247* (2013.01)

(58) Field of Classification Search
USPC .......................................................... 600/301
See application file for complete search history.

(56) References Cited

U.S. PATENT DOCUMENTS

| | | |
|---|---|---|
| 2015/0325004 A1 | 11/2015 | Utsunomiya et al. |
| 2017/0000387 A1 | 1/2017 | Forth et al. |
| 2019/0192013 A1 | 6/2019 | Johanning |

FOREIGN PATENT DOCUMENTS

| | | |
|---|---|---|
| JP | 2016-202871 A | 12/2016 |
| JP | 2017-006305 A | 1/2017 |

OTHER PUBLICATIONS

Written Opinion mailed on Jul. 5, 2019, issued in connection with International Application No. PCT/KR2019/003746, filed on Mar. 29, 2019, 6 pages.

\* cited by examiner

FIGURE 11
FIG. 11A
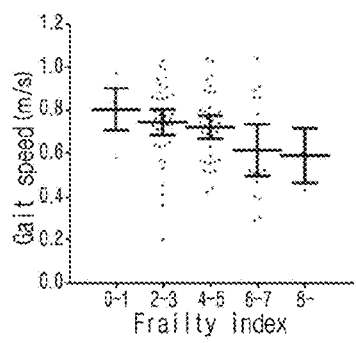
FIG. 11B
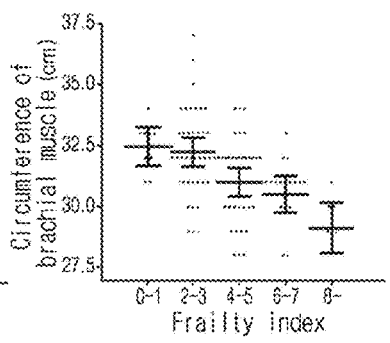
FIG. 11C
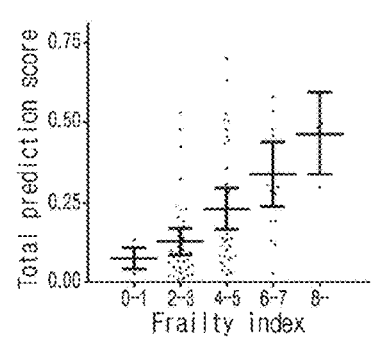

APPARATUS FOR MEASURING DEGREE OF FRAILTY ON BASIS OF ATHLETIC ABILITY PARAMETERS

CROSS REFERENCE TO RELATED APPLICATION

The present application is a continuation of U.S. patent application Ser. No. 16/979,825 filed Mar. 29, 2019, which is a U.S. National Phase Application under 35 U.S.C. 371 of International Application No. PCT/KR2019/003746, filed Mar. 29, 2019, which claims priority to Korean Patent Application No. 10-2018-0039333, filed Apr. 4, 2018, the entire contents of each of which are incorporated herein for all purposes by this reference.

BACKGROUND OF THE INVENTION

Field of the Invention

The present disclosure relates to a method and apparatus for assessment of frailty, and more particularly, to a method and apparatus for assessing frailty index based on the physical performance parameters.

Description of the Related Art

As the population ages, more older patients are undergoing medical care such as chemotherapy that may cause complications, and surgical operations of various severities ranging from minor outpatient surgery to major surgery inevitably requiring intensive postoperative treatment. In such various medical treatments, it is important to assess the physiological functions of patients for preventing complications and unnecessary treatments. However, previous studies have shown that the physiological reserve of patients is not accurately predicted by the chronological ages of the patients. On the contrary, it has been known that the assessment of "frailty," defined as physiological homeostasis deteriorated by aging, is more useful to predict complications, functional disability, mortality, comorbidity, and the outcomes related to medical and surgical treatment than the assessment of chronological ages or classical risk assessment tools.

In general, classical frailty assessing methods, such as comprehensive geriatric assessment (CGA), are performed by assessing individual's nutrition, polypharmacy, activities of daily living (ADL), instrumental activities of daily living (IADL), cognition, mood, social support, physical performance, or the like. However, the comprehensive geriatric assessment requires professionally trained manpower and a long assessment time, and thus, it is difficult to widely use the comprehensive geriatric assessment everywhere other than in specialized geriatric centers. Therefore, there has been an increasing need for a method of quickly and objectively screening frailty during busy outpatient care in various specialized areas for treating older patients.

SUMMARY OF THE INVENTION

The present disclosure provides a frailty diagnosis method of assessing the frailty based on the physical performance parameters. In addition, the present disclosure provides a frailty diagnosis apparatus for performing the frailty diagnosis method. In addition, the present disclosure provides a non-transitory storage medium with a preinstalled program to execute frailty assessment for the frailty diagnosis method.

The present disclosure provides a frailty diagnosis apparatus including a physical performance meter and a processor for determining a frailty index of a target person based on physical performance of the target person obtained by the physical performance meter. The physical performance meter includes at least one among a gait speed meter for measuring a gait speed of the target person, a body balance meter for measuring a body balance maintenance time of the target person, and a muscle strength meter for measuring a muscle exercise time.

In addition, the present disclosure provides a frailty diagnosis method including: measuring, by a gait speed meter, a gait speed of a target person; measuring, by a body balance meter, a body balance maintenance time of the target person; measuring, by a muscle strength meter, a muscle exercise time of the target person; and, determining, by a processor, a frailty index of the target person on the basis of at least one among the gait speed, the body balance maintenance time and the muscle exercise time of the target person that are obtained from the gait speed meter, the body balance meter, and the muscle strength meter, respectively.

Provided is a non-transitory computer-readable recording medium having recorded thereon a program for executing the frailty diagnosis method according to various embodiments of the present disclosure.

According to the frailty diagnosis method and apparatus of the present disclosure, the frailty index of a target person may be rapidly and objectively determined.

BRIEF DESCRIPTION OF THE DRAWINGS

FIG. 11A is a first graph for estimating a frailly index by using a gait speed.

FIG. 11B is a second graph for estimating a frailly index by using a circumference of brachial muscle.

FIG. 11C is a third graph for estimating a frailly index by using a total prediction score.

In the following descriptions of the accompanying drawings, like reference numbers denote like elements unless otherwise specified, and overlapping descriptions thereof are not provided.

DETAILED DESCRIPTION OF THE INVENTION

A frailty diagnosis apparatus is provided. The frailty diagnosis apparatus includes a physical performance meter and a processor for frailty assessment of a target person based on physical performance of the target person obtained by the physical performance meter. The physical performance meter includes at least one among a gait speed meter for measuring a gait speed of the target person, a body balance meter for measuring a body balance maintenance time of the target person, and a muscle strength meter for measuring a muscle exercise time.

Advantages and features of embodiments, and implementation methods thereof will be clarified through the following descriptions given with reference to the accompanying drawings. However, the present disclosure is not limited to the embodiments disclosed below but may be embodied in various forms. Rather, these embodiments are provided so that this disclosure will be thorough and complete, and will fully convey the scope of the present disclosure to those of ordinary skill in the art.

Terms used herein will be briefly described below, and embodiments will be described in detail.

In the present specification, the term "frailty index" refers to an index indicating the degree of facility of older adults. The frailty index of an individual is expressed by the ratio of the number of frailty-related symptoms that the individual has to the total number of frailty-related symptoms. Therefore, when an individual has no frailty-related symptoms, the frailty index of the individual is 0, and on the contrary, when an individual has all the frailty-related symptoms, the frailty index of the individual is 1. In other words, when an older person has a high frailty index, the individual has a severe degree of frailty. The number and types of symptoms used to measure the frailty index may be adjusted by a meter.

In the present specification, the term "cohort" refers to a group who shares a certain statistical factor. Cohort studies may be conducted to track the incidence of a disease of concern depending on a factor by comparing a group exposed to the factor with a group not exposed to the factor. For example, cohort studies may be conducted to track the survival rates of groups classified according to the gait speeds or frailty indexes thereof.

Figure 1:
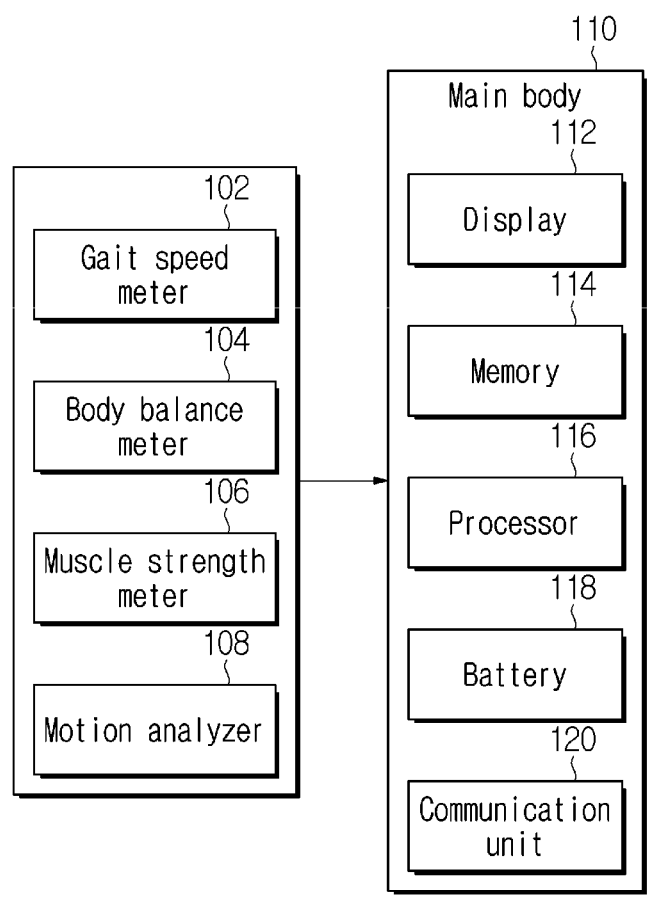
FIG. 1 illustrates an embodiment of a frailty diagnosis apparatus for assessing frailty index of a target person.

FIG. 1 illustrates an embodiment of a frailty diagnosis apparatus 100 for predicting a frailty index of a target person.

The frailty diagnosis apparatus 100 may include the gait speed meter 102, the body balance meter 104, the muscle strength meter 106, the motion analyzer 108, and/or the main body 110. The main body 100 may be connected to the gait speed meter 102, the body balance meter 104, the muscle strength meter 106, and/or the motion analyzer 108, thereby obtaining information required for determining a frailty index. FIGS. 3 to 6 illustrate functions of the gait speed meter 102, the body balance meter 104, the muscle strength meter 106, and/or the motion analyzer 108. Depending on embodiments, an additional configuration for assessing a frailty index may be installed in the frailty diagnosis apparatus 100.

The main body 110 may include a communication unit 112 for receiving information from the gait speed meter 102, the body balance meter 104, the muscle strength meter 106, and/or the motion analyzer 108. The communication unit 112 may restore information obtained by the gait speed meter 102, the body balance meter 104, the muscle strength meter 106, and/or the motion analyzer 108 by demodulating and decoding signals transmitted from the gait speed meter 102, the body balance meter 104, the muscle strength meter 106, and/or the motion analyzer 108.

The main body 110 may include a memory 114 to storing information obtained from the communication unit 112 and/or information processed by the processor 116. In addition, the memory 114 may store, for information processing of the processor 116, information on a gait speed parameter, a body balance parameter and a muscle strength parameter, a database on a gait speed-frailty index correlation, a body balance maintenance time-frailty index correlation and a muscle exercise time-frailty index correlation, information on walking motion analysis data for a target person, and information for determining a frailty index based on a combination of a body balance maintenance time, a muscle exercise time and other measurement values.

The main body 110 may include the processor 116 for determining a frailty index of a target person based on information obtained from the gait speed meter 102, the body balance meter 104, the muscle strength meter 106 and/or the motion analyzer 108. The processor 116 may determine a frailty index of a target person by using not only a database stored in the memory 114 but also a database stored outside of the main body 110. The processor 116 may reflect a diagnosis result of a target person in a database stored in the memory 114 or in an external memory of the main body 110. Two or more processors 116 may be provided. When more than one processor is used, the processors need not to be physically adjacent to each other.

The processor 116 may determine the frailty index of the target person 170 based on the gait speed of the target person 170. The processor 116 may calculate the physiological age of the target person 170 according to the gait speed of the target person 170 with reference to a correlation between gait speed and frailty index.

The processor 116 may determine a gait speed parameter representing the gait speed. The gait speed parameter represents a gait speed in a specific section. For example, the gait speed parameter may be defined for each section having a size of 0.2 m/s. In a specific example, the gait speed parameter may be defined as 1 for a section of 0.4 m/s to 0.6 m/s and as 2 for a section of 0.6 m/s to 0.8 m/s. In addition, the gait speed parameter may be defined for the rest sections each having a size of 0.2 m/s. The above example is merely an illustrative example, and values of the gait speed parameter and sections corresponding thereto may be easily changed by those of ordinary skill in the art.

Likewise, the processor 116 may determine a body balance maintenance time parameter indicating a body balance maintenance time and a muscle exercise time parameter indicating a muscle exercise time. A body balance maintenance time parameter represents a body balance maintenance time in a specific interval, and a required time parameter for muscle exercise represents a required time of muscle exercise in a specific interval. A required time parameter for muscle exercise and a body balance maintenance time parameter may be defined in each interval of seconds.

In addition, the processor 116 may determine a motion parameter of the target person 170 generated by motion capture. Also, the processor 116 may define data required for a frailty index in each interval.

The processor 116 may predict a frailty index based on the gait speed with reference to a gait speed-frailty index correlation indicating a relationship between gait speed and frailty index. When the gait speed is expressed by the gait speed parameter, the processor 116 may determine a frailty index based on the gait speed parameter with reference to the gait speed-frailty index correlation. The gait speed-frailty index correlation may be determined by regression analysis of statistical data about gait speeds and frailty indexes. The gait speed-frailty index correlation will be specifically explained in the description of FIGS. 3A and 3B.

Likewise, the processor 116 may predict a frailty index from a body balance maintenance time based on a body balance maintenance time-frailty index correlation indicating a relationship between a body balance maintenance time and a frailty index. In addition, the processor 116 may predict a frailty index based on a muscle exercise time-frailty index correlation. In addition, the processor 116 may predict a frailty index based on a correlation between a multiplicity of motion parameters of the target person 170 and a frailty index.

In addition, when a multiplicity of elements is considered for predicting a frailty index, the processor 116 may predict the frailty index based on a multiple correlation between the frailty index, on the one hand, and a gait speed, a body balance maintenance time, a muscle exercise time and other elements, on the other hand.

The processor 116 may derive the health state of the target person 170 based on the physiological age of the target person 170 determined based on the frailty index of the target person 170, the actual age and gender of the target person 170, etc. The processor 116 may calculate information such as postoperative mortality and postoperative complication rates according to information such as the frailty index. Therefore, the processor 116 may help users of the frailty diagnosis apparatus 100 in determining treatment methods for the target person 170.

The main body 110 may include the battery 118 that stores electrical energy for smooth operations of the elements of the main body 110. The battery 118 may include a charger that receives electrical energy from the outside of the main body 110. In addition, the battery 118 may include a voltage regulator to supply an appropriate voltage to the elements of the main body 110.

The main body 110 may include the display 120, which displays results of calculation of the processor 116. For example, the display 120 may display values measured or calculated by the frailty diagnosis apparatus 100, such as a gait speed parameter, body balance parameter, a muscular strength parameter and a frailty index. The main body 110 may further comprise more elements for frailty index assessment.

Figure 2:
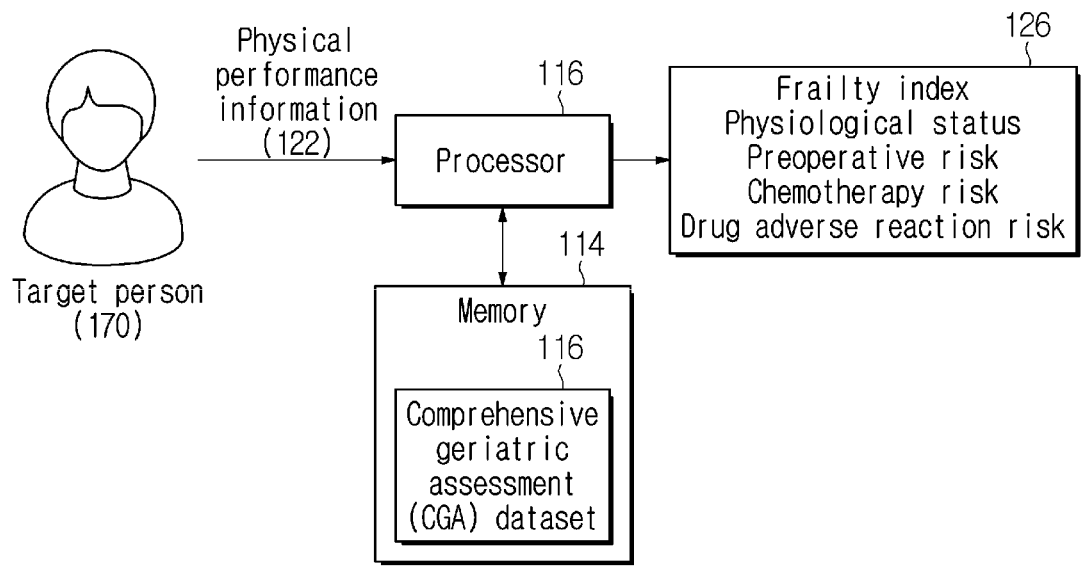
FIG. 2 is a conceptual diagram for explaining a frailty diagnosis process.

FIG. 2 is a conceptual diagram for explaining a frailty diagnosis process. In a short physical performance battery (SPPB), the walking ability, body balance and/or muscle strength of the target person 170 are measured to simply measure a frailty index. A method of measuring the walking ability, body balance and/or muscle strength of the target person 170 is described with reference to FIGS. 3 to 5.

Physical performance information 122 includes information on walking ability, body balance, and/or muscle strength. Apart from information used in the SPPB, information on other physical abilities of the target person 170 may be included in the physical performance information 122. The processor 116 of the main body 110 may analyze the physical performance information 122 according to the Comprehensive Geriatric Assessment (CGA) dataset 124 stored in the memory 114. The processor may generate target person information 126 according to an analysis result of the physical performance information 122. The target person information 126 may include not only a frailty index of the target person but also information on a physiological status, a preoperative risk, a chemotherapy risk, and a drug adverse reaction risk.

Figure 3:
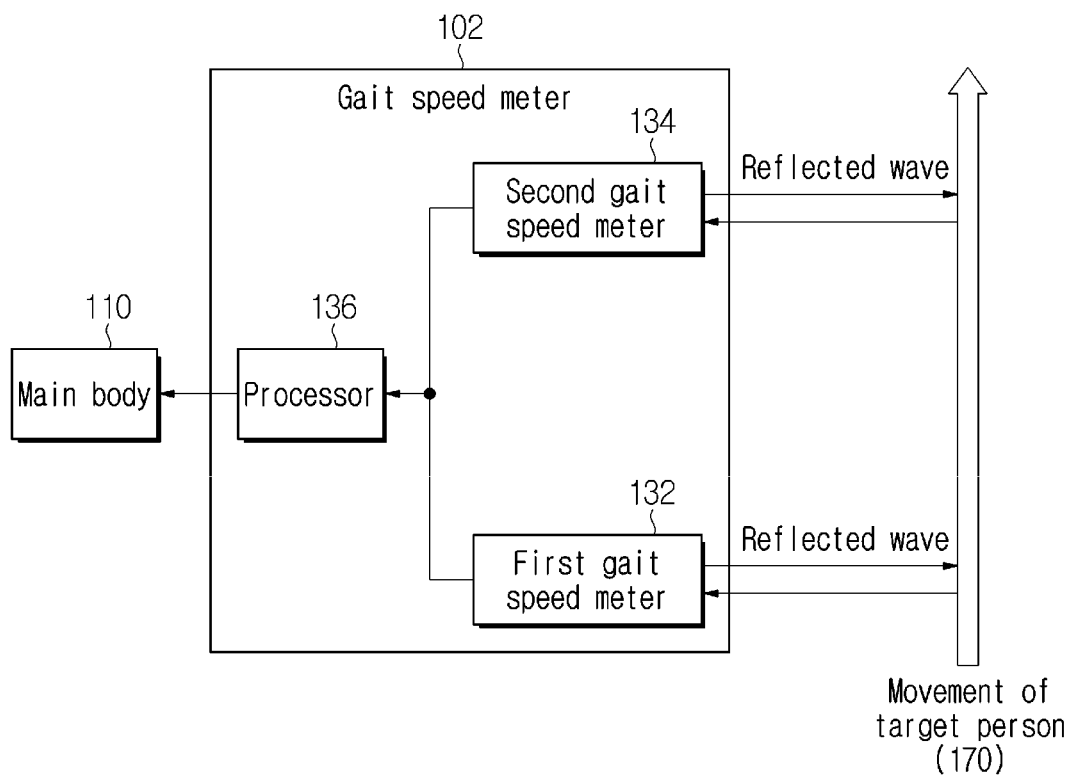
FIG. 3 illustrates an embodiment of a gait speed meter 102 for measuring the walking ability of a target person 170.

FIG. 3 illustrates an embodiment of a gait speed meter 102 for measuring the gait speed of the target person 170.

The gait speed meter 102 may include a first gait speed meter 132, a second gait speed meter 134, and a processor 136. In addition, the gait speed meter 102 may further include another gait speed meter. In addition, the gait speed meter 102 may further include an apparatus required for measuring a gait speed.

The first gait speed meter 132 and the second gait speed meter 134 detect a movement of the target person 170. The first gait speed meter 132 and the second gait speed meter 134 may emit a laser beam or ultrasonic waves and recognize reflected laser beam or ultrasonic waves. In addition, the first gait speed meter 132 and the second gait speed meter 134 may detect a movement of the target person 170 based on a recognized laser or ultrasonic signal.

When detecting a movement of the target person 170, the first gait speed meter 132 and the second gait speed meter 134 may transmit a detection time to the processor 136. Information transmitted to the processor 136 from the first gait speed meter 132 and the second gait speed meter 134 may be distinguished by a separate identifier.

The first gait speed meter 132 and the second gait speed meter 134 periodically check a relative distance. The first gait speed meter 132 and the second gait speed meter 134 may periodically transmit a relative distance to the processor 136. In addition, the first gait speed meter 132 and the second gait speed meter 134 may transmit a distance between the target person 130 and the first gait speed meter 132 and a distance between the target person 130 and the second gait speed meter 134 to the processor 136.

The processor 136 may set a setting value for measuring a gait speed according to a position of the first gait speed meter 132 or the second gait speed meter 134. For example, the processor 136 may calculate a relative distance between the first gait speed meter 132 and the second gait speed meter 134 according to positions of the first gait speed meter 132 and the second gait speed meter 134.

In one embodiment, the processor 136 may periodically set a setting value according to a setting cycle. In another embodiment, the processor 136 may set a setting value, when at least one among the first gait speed meter 132 and the second gait speed meter 134 changes a position. By setting a setting value either periodically or when a change of position is detected, the processor 136 may reflect position changes of the first gait speed meter 132 and the second gait speed meter 134.

The processor 136 may calculate a gait speed of the target person 170 based on at least one setting value. For example, the processor 136 may calculate a gait speed based on a set relative distance. Specifically, the processor 136 may calculate a gait speed of the target person 130 by dividing a set relative distance by a difference of detection time between the first gait speed meter 132 and the second gait speed meter 134.

Considering distances between the target person 130, on the one hand, and the first gait speed meter 132 and the second gait speed meter 134 respectively, on the other hand, the processor 136 may adjust a relative distance between the first gait speed meter 132 and the second gait speed meter 134. Due to a mismatch of measurement angle between the first gait speed meter 132 and the second gait speed meter 134, an actual travel distance of the target person 130 may be distorted. Accordingly, when the first gait speed meter 132 and the second gait speed meter 134 are installed in parallel and a relative distance is adjusted, an actual travel distance of the target person 130 may be exactly calculated.

In FIG. 3, the main body 110 is physically separated from the gait speed meter 102. However, according to an embodiment, the main body 110 may be physically coupled to the gait speed meter 102. In FIG. 3, the processor 136 may be included in the gait speed meter 102. However, according to an embodiment, the processor 136 may be omitted from the gait speed meter 102. Accordingly, the function of the processor 136 may be performed by the processor 116 of the main body 110.

Figure 4:
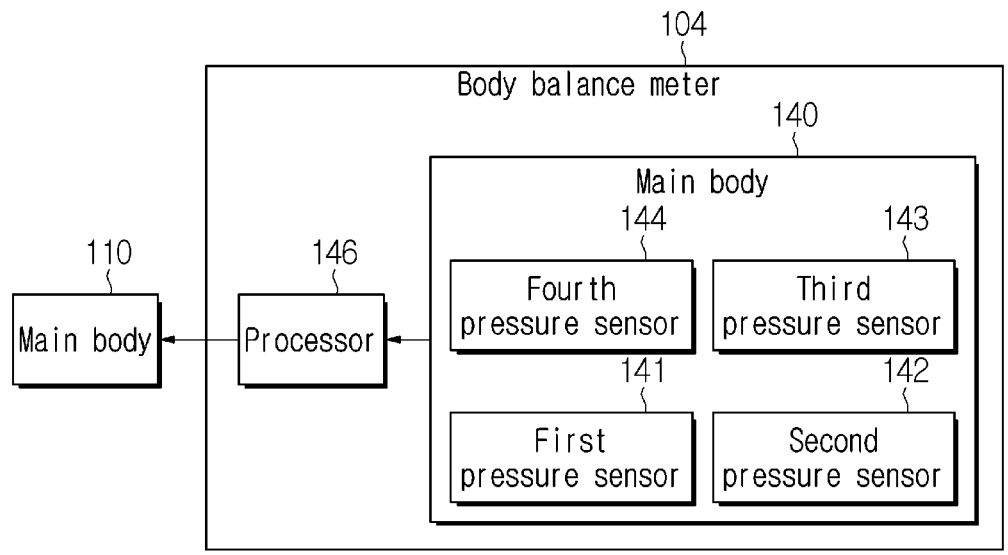
FIG. 4 illustrates an embodiment of a body balance meter 104 for measuring the body balance of the target person 170.

FIG. 4 illustrates an embodiment of a body balance meter 104 for measuring the body balance of the target person 170.

The body balance meter 104 may include a body balance measurement platform 140 and a processor 146. In addition, according to an embodiment, the body balance meter 104 may further include an apparatus required for measuring a body balance maintenance time.

The body balance measurement platform 140 may include four pressure sensors 141, 142, 143, 144. Each pressure sensor of the body balance measurement platform 140 may detect a pressure caused by a weight of the target person 170 and transmit a pressure maintenance time to the processor 146.

The body balance measurement platform 140 may measure body balance maintenance times for side-by-side stance, semi-tandem stance, and tandem stance.

The side-by-side stance is a stance where both feet are parallel to each other. A body balance time for a side-by-side stance may be measured by measuring a time where the target person 170 maintains a pressure for the first pressure sensor 141 and the second pressure sensor 142 using both feet. Alternatively, in order to measure a body balance time for a side-by-side stance, the third pressure sensor 143 and the fourth pressure sensor 144 may be used.

The semi-tandem stance is a stance where both feet are diagonal to each other. A body balance time for a semi-tandem stance may be measured by measuring a time where the target person 170 maintains a pressure for the first pressure sensor 141 and the third pressure sensor 143 using both feet. Alternatively, in order to measure a body balance time for a semi-tandem stance, the second pressure sensor 142 and the fourth pressure sensor 144 may be used.

The tandem stance is a stance where feet are placed heel to toe. A body balance time for a tandem stance may be measured by measuring a time where the target person 170 maintains a pressure for the first pressure sensor 141 and the fourth pressure sensor 144 using both feet. Alternatively, in order to measure a body balance time for a tandem stance, the second pressure sensor 142 and the third pressure sensor 143 may be used.

The processor 146 may recognize a stance of the target person 170 and determine a body balance maintenance time for the stance of the target person 170 according to signals of pressure sensors. Alternatively, the processor 146 may receive an input of stance to be taken by the target person 170 according to an experimenter's operation and determine a body balance maintenance time for the stance of the target person 170.

According to an embodiment, the body balance measurement platform 140 may be designed to include two or three pressure sensors or five or more pressure sensors.

In FIG. 4, the main body 110 is physically separated from the body balance meter 104. However, according to an embodiment, the main body 110 may be physically coupled to the body balance meter 104. In FIG. 4, the processor 146 may be included in the body balance meter 104. However, according to an embodiment, the processor 146 may be omitted from the body balance meter 104. Accordingly, the function of the processor 146 may be performed by the processor 116 of the main body 110.

Figure 5:
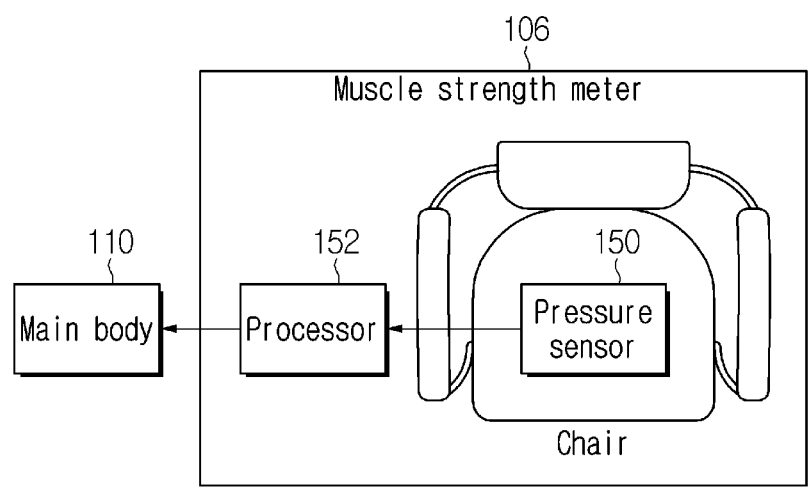
FIG. 5 illustrates an embodiment of a muscle strength meter 106 for measuring muscle strength of the target person 170.

FIG. 5 illustrates an embodiment of a muscle strength meter 106 for measuring muscle strength of the target person 170.

The muscle strength meter 106 may include a pressure sensor 150 and a processor 152. In addition, according to an embodiment, the muscle strength meter 106 may further include an apparatus for measuring a muscle exercise time.

In order to measure the muscle strength of the target person 170, the target person 170 repeat to sit in and stand up from a chair equipped with a pressure sensor 150 for a predetermined number of times. The processor 152 may determine the predetermined number of times.

When detecting a pressure caused by a weight of the target person 170, the pressure sensor 150 may transmit a pressure signal to the processor 152. When receiving the pressure signal of the target person 170 from the pressure sensor 150, the processor 152 measures a time taken for the target person 170 to sit in and stand up for the predetermined number of times. In addition, the processor 152 may transmit the measured time to the main body 110.

In FIG. 5, the main body 110 is physically separated from the muscle strength meter 106. However, according to an embodiment, the main body 110 may be physically coupled to the muscle strength meter 106. In FIG. 5, the processor 152 may be included in the muscle strength meter 106. However, according to an embodiment, the processor 152 may be omitted from the muscle strength meter 106. Accordingly, the function of the processor 152 may be performed by the processor 116 of the main body 110.

Figure 6:
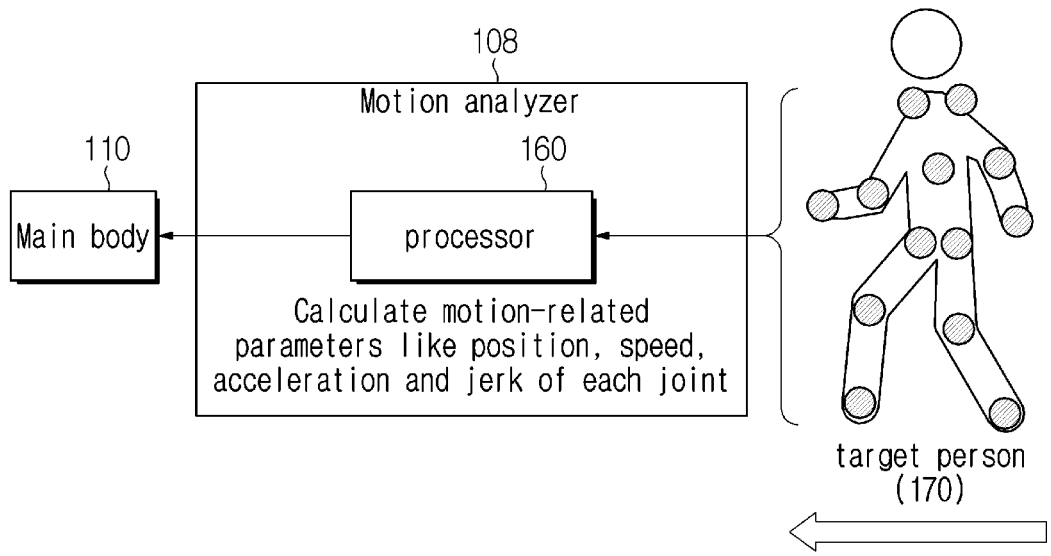
FIG. 6 illustrates an embodiment of a motion analyzer 108 for analyzing a walking motion of the target person 170.

FIG. 6 illustrates an embodiment of a motion analyzer 108 for analyzing a walking motion of the target person 170.

A motion analyzer may record a motion of the target person 170 by using a motion capture software. A processor 160 included in the motion analyzer 108 obtains a motion parameter by analyzing movements of each joint and a degree of movement in an upper body while the target person 170 is walking. The motion parameter includes a position, a velocity, an acceleration, and a jerk of each joint landmark.

The motion parameter is transmitted to the main body 110 and used to analyze a frailty index of the target person 170, along with a gait speed obtained from the gait speed meter 102 in FIG. 3. Specifically, based on a motion parameter and a gait speed, a physical frailty index, a cognitive function index and/or a fall risk may be predicted.

In FIG. 6, the main body 110 is physically separated from the motion analyzer 108. However, according to an embodiment, the main body 110 may be physically coupled to the motion analyzer 108. In FIG. 6, the processor 160 may be included in the motion analyzer 108. However, according to an embodiment, the processor 160 may be omitted from the motion analyzer 108. Accordingly, the function of the processor 160 may be performed by the processor 116 of the main body 110.

The processor 116 may determine a frailty index by using not only indexes measured in FIGS. 3 to 6 but also other measurements. In order to measure a frailty index, an additional factor may be used along with a gait speed. For example, a physical frailty index, a cognitive frailty/function index, and a biomarker may be additionally considered.

The processor 116 may perform the calculation based on statistical data. For example, statistical data about the above-described gait speed-frailty index correlation may be used. In addition, statistical data according to gait speeds and the actual age and gender of the target person 130 may be used. In addition, statistical data about other factor related to a frailty index may be used.

Figure 7:
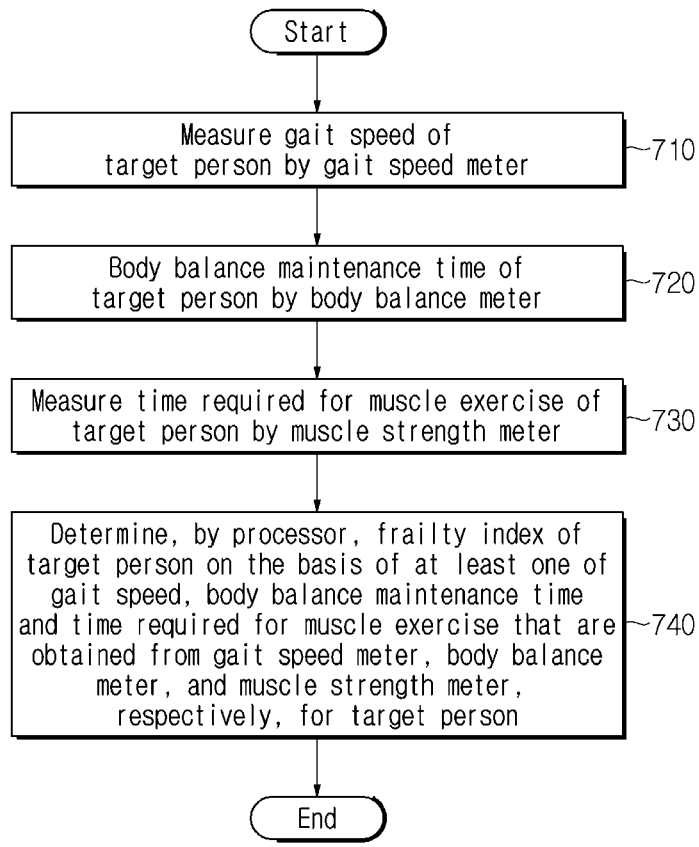
FIG. 7 illustrates an embodiment of a frailty diagnosis method for assessing frailty index of a target person.

FIG. 7 illustrates an embodiment of a frailty diagnosis method for determining a frailty index based on a gait speed of a target person.

In the step S710, a gait speed of the target person 170 may be measured using the gait speed meter 102. As two or more gait detection sensors of the gait speed meter 102 detect a movement of the target person 170, a gait speed of the target person 170 may be calculated. In addition, by the gait speed meter 102, output information recording at least one among detection time and distance of the target person 170 may be output.

In the step S720, the body balance meter 104 may measure a body balance maintenance time of the target person 170. A pressure of the target person 170 is detected by a body balance measurement platform including four or more pressure sensors in the body balance meter 104. In addition, the body balance meter 104 may determine a duration of the pressure of the target person 170 upon the sensors as a body balance maintenance time. The body balance meter 104 may classify and determine body balance maintenance times for side-by-side stance, semi-tandem stance, and tandem stance.

In the step S730, the muscle strength meter 106 may measure a muscle exercise time for the target person 170. A pressure sensor included in the muscle strength meter 106 may detect a pressure caused by an action of the target person 170. In addition, the muscle strength meter 106 may determine a time for the pressure sensor to detect a predetermined number of the pressures as a muscle exercise time.

In the step S740, the processor 116 may determine a frailty index of the target person 170 based on at least one among a gait speed, a body balance maintenance time and a muscle exercise time that are obtained from a gait speed meter, a body balance meter, and a muscle strength meter, respectively, for the target person 170.

In addition, the processor 116 may express a gait speed, a body balance maintenance time, and/or a muscle exercise time as a gait speed parameter, a body balance maintenance time parameter, and/or a muscle exercise time parameter respectively, depending on which section the gait speed, the body balance maintenance time and/or the muscle exercise time are included in. In addition, the processor 116 may predict a frailty index of the target person 170, depending on correlation functions between a frailty index, on the one hand, and a gait speed or a gait speed parameter, a body balance maintenance time or a body balance maintenance time parameter, and a muscle exercise time or a parameter of a muscle exercise time, respectively, on the other hand.

Apart from a gait speed, a body balance maintenance time and a muscle exercise time, other factors may be additionally measured or obtained to predict a frailty index. In addition, a frailty index may be predicted by using a gait speed, a body balance maintenance time, and a muscle exercise time, along with additional factors. For example, the additional factors may include a motion parameter of the target person 170 obtained from the motion analyzer 108.

A frailty index calculated by the processor 116 may include a physical frailty index, a cognitive frailty index, and a fall risk. In addition, a physical frailty index, a cognitive frailty index and a fall risk may be calculated in different ways. The processor 116 may use a frailty index to derive not only an age and a gender but also a health state of the target person 170.

In order to implement the frailty diagnosis method of FIG. 7, not only the above-described embodiment but also the function of the frailty diagnosis apparatus 100 in FIG. 1 and functions of the meters described in FIGS. 3 to 6 may be applied to the frailty diagnosis method of FIG. 7.

Figure 8A:
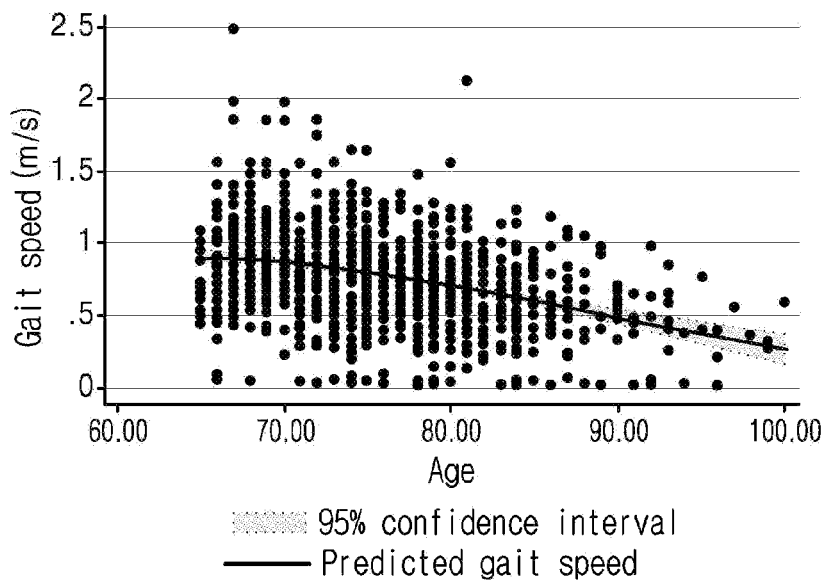
FIGS. 8A and 8B are two-dimensional graphs respectively illustrating a relationship between actual age and gait speed and a relationship between frailty and gait speed.
Figure 8B:

FIGS. 8A and 8B are two-dimensional graphs respectively illustrating a relationship between chronological age and gait speed and a relationship between frailty index and gait speed. The graphs of FIGS. 8A and 8B were obtained through linear regression analysis of statistical data, and the relationship between chronological age and gait speed and the relationship between frailty index and gait speed are shown in the form of a linear function in FIGS. 8A and 8B.

The x-axis in FIG. 8A refers to an average gait speed in m/s. In addition, the y-axis in FIG. 8A refers to actual age. Referring to FIG. 8A, it may be seen that the average gait speed decreases as the actual age increases. Therefore, it may be seen that the gait speed has a correlation with frailty.

The x-axis in FIG. 8B refers to an average gait speed in m/s. In addition, the y-axis in FIG. 8B refers to a frailty index. Referring to FIG. 8B, it may be seen that the average gait speed decreases as the frailty index increases. Therefore, it may be seen that the gait speed has a correlation with frailty.

Therefore, referring to FIGS. 8A and 8B, the physiological age and frailty index of a target person may be estimated by measuring the gait speed of the target person.

Figure 9:
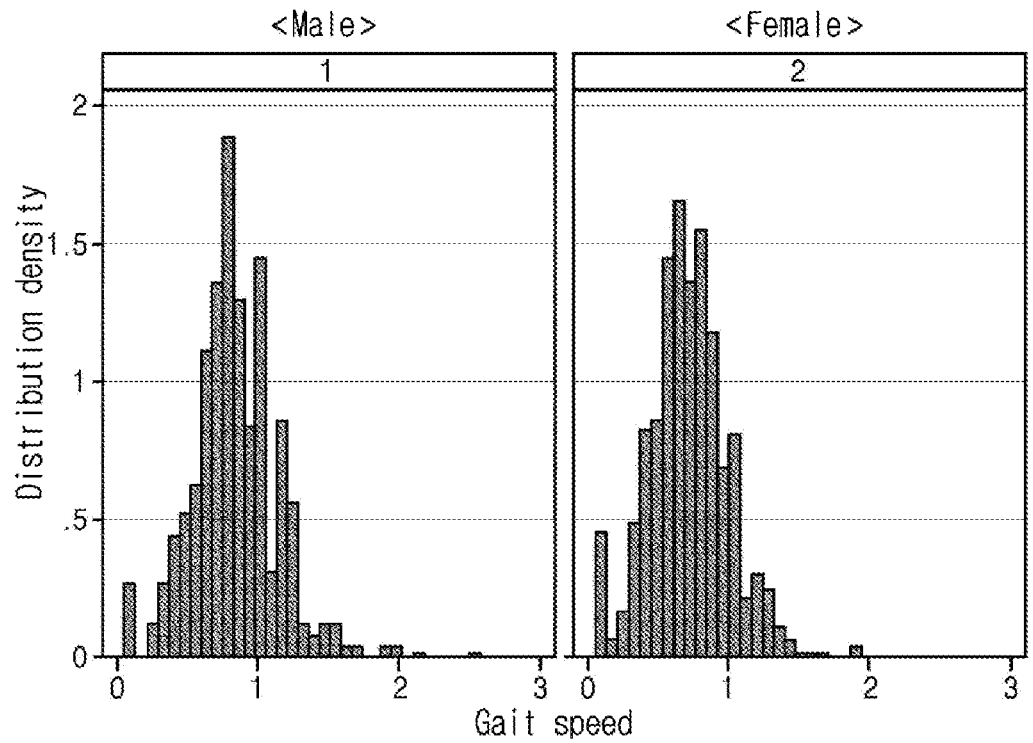
FIG. 9 is a graph illustrating the mortality of groups having certain gait speeds by Kaplan-Meier analysis.

FIG. 9 is a graph illustrating the survival probabilities of groups having certain gait speeds by Kaplan-Meier analysis. Kaplan-Meier analysis concerns the probability of survival over time of people having specific conditions, which may be obtained by observing a sufficiently large sample population for a long period of time.

The x-axis in FIG. 9 refers to the proportion of survivors to the total cohort participants, and the y-axis in FIG. 9 refers to a measurement period Referring to FIG. 9, the cohort participants are classified into four groups 910, 920, 930, and 940 according to the gait speeds thereof, and results of observation of deaths over the measurement period are shown for each group. The proportion of survivors in the group 940 having the lowest gait speed has decreased the most, and the proportion of survivors in the group 910 having the highest gait speed has decreased the least. That is, the higher gait speed the group has, the higher survival rate the group has.

Therefore, the frailty diagnosis apparatus 100 may estimate the survival probability of a target person by measuring the gait speed of the target person.

Table 1 below shows items strongly related to the gait speed. When a population group is divided into participants (high speed walkers) who walk faster than the median speed and participants (low speed walkers) who walk slower than the median speed, statistically significant differences are observed therebetween in multimorbidity, grip strength, short physical performance battery (SPPB), frailty indexes (K-FRAIL and OHS frailty score), activities of daily living and instrumental activities of daily living (ADL, IADL), depression, cognition, polypharmacy, fall history, etc. That is, it is possible to infer the health state of a target person by measuring the gait speed of the target person.

TABLE 1

| Items | Low speed walkers | High speed walkers | P value |
|---|---|---|---|
| multimorbidity (n) | 310.00 | 221.00 | <0.001 |
| Dominant grip strength (mean, sd) | 19.92 | 24.90 | <0.001 |
| SPPB score (mean, sd) | 6.61 | 9.37 | <0.001 |
| K-FRAIL score (mean, sd) | 1.63 | 0.93 | <0.001 |
| CHS score (mean, sd) | 2.39 | 1.25 | <0.001 |
| ADL disability (n, %) | 125.00 | 56.00 | <0.001 |
| IADL disability (n, %) | 294.00 | 150.00 | <0.001 |
| Depression (n, %) | 102.00 | 34.00 | <0.001 |
| Cognitive dysfunction (n, %) | 270.00 | 125.00 | <0.001 |
| Polypharmacy (n, %) | 193.00 | 113.00 | <0.001 |
| Fall history for previous 1 year (mean, sd) | 0.33 | 0.16 | 0.001 |

Figure 10:
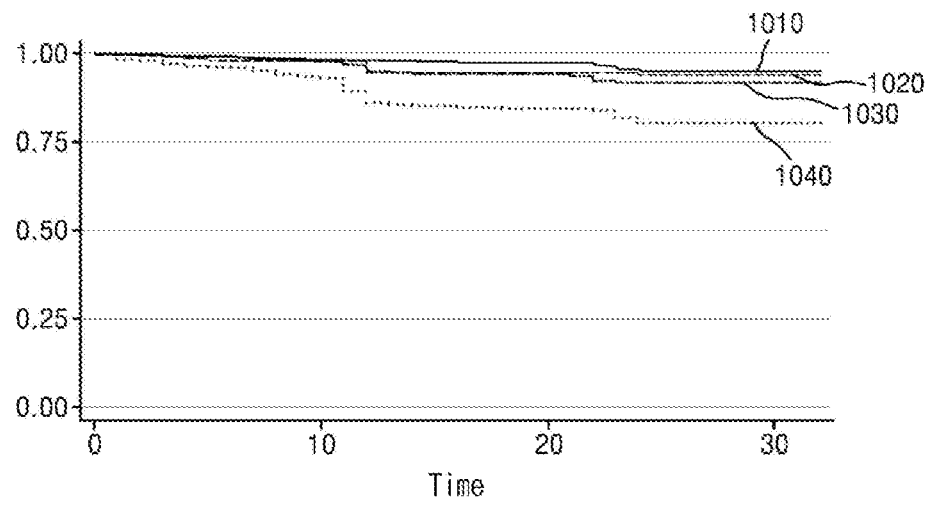
FIG. 10 illustrates distributions of the gait speed of community dwelling older in Korea according to the genders.
Figure 10:
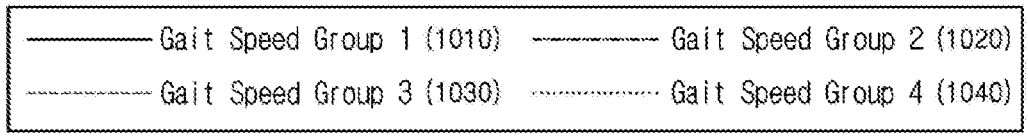

FIG. 10 illustrates distributions of the gait speed of community dwelling older adults in Korea according to the genders. The left graph in FIG. 10 shows a distribution of the gait speed of men. The right graph in FIG. 10 shows a distribution of the gait speed of women. Since there is a difference in the distribution of gait speed between men and women, it is necessary to consider the gender of a target person in addition to the gait speed of the target person when measuring the physiological age of the target person.

FIG. 11A, FIG. 11B, and FIG. 11C are graphs for estimating a frailty index by using a gait speed and other measured values. The gait speed and the circumference of *brachialis* are measured to show a correlation between the frailty index and the sum of a gait speed parameter and a *brachialis* circumference parameter. The *brachialis* circumference parameter is related to the muscle function of a target person and is thus closely related to the frailty index of the target person. Thus, the *brachialis* circumference parameter is an important factor together with the gait speed when estimating a frailty index.

The graph of FIG. 11A shows a correlation between the gait speed parameter and the frailty index. Referring to the graph of FIG. 11A, as the gait speed parameter decreases, the frailty index increases.

The graph of FIG. 11B shows a correlation between the *brachialis* circumference parameter and the frailty index. Referring to the graph of FIG. 11B, as the *brachialis* circumference parameter decreases, the frailty index increases.

The graph of FIG. 11C shows a correlation between the frailty index and an evaluation value obtained based on the gait speed parameter and the *brachialis* circumference parameter according to the results shown in the graphs of FIG. 11A, FIG. 11B, and FIG. 11C. Referring to the graphs of FIG. 11 A, FIG. 11B, and FIG. 11C, as the evaluation value increases, the frailty index increases. The accuracy of estimation of a frailty index may increase by considering two or more factors in combination. As shown, the evaluation value obtained by combining the gait speed and the brachial circumference is used. However, another factor may be used instead of or in addition to the *brachialis* circumference to estimate the frailty index.

Embodiments have been described above in detail with reference to the accompanying drawings so that those of ordinary skill in the art may easily implement the present disclosure. In the drawings, portions not related to the present disclosure are omitted for clarity of description.

The above-described embodiments may be written as computer-executable programs and may be implemented in general-purpose digital computers that execute the programs using a non-transitory computer-readable recording medium.

The terms used in the present specification are selected based on general terms currently widely used in the art in consideration of functions regarding the present disclosure, but the terms may vary according to the intention of those of ordinary skill in the art, precedents, or new technology in the art. Also, some terms may be arbitrarily selected by the applicants, and in this case, the meaning of the selected terms are described in the detailed description of the present disclosure. Thus, the terms used herein should not be construed based on only the names of the terms but should be construed based on the meaning of the terms together with the description throughout the present disclosure.

The terms of a singular form may include plural forms unless referred to the contrary. In the present specification, when it is described that a part or portion "includes" and/or "comprises" a particular element, the presence or addition of one or more other elements in the part or portion is not precluded, and the part or portion may include or comprise one or more other elements unless otherwise specified.

While some best embodiments of the present disclosure have been described, it will be apparent to those of ordinary skill in the art that substitutions, modifications, and changes may be made therefrom. That is, the claims may include all such substitutions, modifications, and changes. Therefore, all described in the present specification including the drawings should be construed in an illustrative and non-limiting sense.

What is claimed is:

1. A diagnosis apparatus for prediction or evaluation of a health state, the apparatus comprising:
   a physical performance test instrument comprising at least one among a gait speed test instrument to measure a gait speed of a target person, a balance test instrument to measure a balance maintenance time of the target person, and a muscle performance test instrument to measure a muscle movement of the target person; and
   a processor configured to determine a SPPB (Short Physical Performance Battery) result based on gait speed, balance maintenance time, and muscle movement of the target person obtained by the physical performance test instrument,
   wherein the balance test instrument determines balance maintenance times for at least one of side-by-side stance, semi-tandem stance, and tandem stance.

2. The diagnosis apparatus of claim 1, wherein the balance test instrument comprises a balance measurement platform comprising four or more pressure sensors and measures forces induced to the pressure sensors by the target person as a balance maintenance time.

3. A diagnosis apparatus for prediction or evaluation of a health state, the apparatus comprising:
   a physical performance test instrument comprising at least one among a gait speed test instrument to measure a gait speed of a target person, a balance test instrument to measure a balance maintenance time of the target person, and a muscle performance test instrument to measure a muscle movement of the target person; and
   a processor configured to determine a SPPB (Short Physical Performance Battery) result based on gait speed, balance maintenance time, and muscle movement of the target person obtained by the physical performance test instrument,
   wherein the muscle performance test instrument comprises a pressure sensor configured to detect a pressure according to an action of the target person and determines either or both force and time induced to the pressure sensor in order to detect sit-to-stand movements.

4. The diagnosis apparatus of claim 3, wherein the muscle performance test instrument comprises a range sensor configured to detect a range according to an action of the target person and determines a distance apart from the range sensor to detect the sit-to-stand movements.

5. The diagnosis apparatus of claim 4, wherein the sit-to-stand movements consist of sitting movement phases and standing movement phases, and
wherein the timings of sitting movement phases are derived by force and time induced by the pressure sensor, and the timings of standing movement phases are derived by a distance apart from the range sensor.

6. A diagnosis apparatus for prediction or evaluation of a health state, the apparatus comprising:
a physical performance test instrument comprising at least one among a gait speed test instrument to measure a gait speed of a target person, a balance test instrument to measure a balance maintenance time of the target person, and a muscle performance test instrument to measure a muscle movement of the target person; and
a processor configured to determine a SPPB (Short Physical Performance Battery) result based on gait speed, balance maintenance time, and muscle movement of the target person obtained by the physical performance test instrument,
wherein the processor obtains a gait speed parameter from the gait speed obtained from the gait speed test instrument, a balance parameter from the balance maintenance time obtained from the balance test instrument, and the muscle performance parameter from the muscle movement obtained from the muscle performance test instrument, and
wherein the processor determines a SPPB result from at least one of parameters including the gait speed parameter, the balance parameter, and the muscle performance parameter,
wherein the gait speed parameter represents a gait speed in a predetermined interval,
wherein the balance parameter represents a balance maintenance time in predetermined stances, and
wherein the muscle performance parameter represents time for sit-to-stand movements in a predetermined count.

7. A diagnosis method for prediction or evaluation of a health state, the method comprising:
measuring, by a gait speed test instrument, a gait speed of a target person;
measuring, by a balance test instrument, a balance maintenance time of the target person;
measuring, by a muscle performance test instrument, a muscle movement of the target person; and
determining, by a processor, a SPPB result of the target person on the basis of at least one among the gait speed, the balance maintenance time and the muscle movement of the target person that are respectively obtained from the gait speed test instrument, the balance test instrument, and the muscle performance test instrument,
wherein the balance test instrument determines balance maintenance times for at least one of side-by-side stance, semi-tandem stance, and tandem stance.

8. The diagnosis method of claim 7, wherein the balance maintenance time is determined based on durations of forces caused by the target person upon four or more pressure sensors on a body balance measurement platform in the balance test instrument.

9. A diagnosis method for prediction or evaluation of a health state, the method comprising:
measuring, by a gait speed test instrument, a gait speed of a target person,
measuring, by a balance test instrument, a balance maintenance time of the target person,
measuring, by a muscle performance test instrument, a muscle movement of the target person; and
determining, by a processor, a SPPB result of the target person on the basis of at least one among the gait speed, the balance maintenance time and the muscle movement of the target person that are respectively obtained from the gait speed test instrument, the balance test instrument, and the muscle performance test instrument,
wherein sit-to-stand movements is determined based on either or both force and time induced to a pressure sensor,
wherein the pressure sensor is included in the muscle performance test instrument and is configured to detect pressure according to an action of the target person.

10. The diagnosis method of claim 9, the sit-to-stand movements is detected by determining a distance apart from a range sensor and the range sensor is included in the muscle performance test instrument and is configured to detect a range according to the action of the target person.

11. The diagnosis method of claim 10, wherein the sit-to-stand movements consist of sitting movement phases and standing movement phases, and
wherein the timings of sitting movement phases are derived by force and time induced by the pressure sensor, and the timings of standing movement phases are derived by a distance apart from the range sensor.

12. A diagnosis method for prediction or evaluation of a health state, the method comprising:
measuring, by a gait speed test instrument, a gait speed of a target person;
measuring, by a balance test instrument a balance maintenance time of the target person;
measuring, by a muscle performance test instrument, a muscle movement of the target person; and
determining, by a processor, a SPPB result of the tar et person on the basis of at least one among the gait speed, the balance maintenance time and the muscle movement of the target person that are respectively obtained from the gait speed test instrument, the balance test instrument, and the muscle performance test instrument,
wherein a gait speed parameter is obtained from the gait speed obtained from the gait speed test instrument, a body balance parameter is obtained from the body balance maintenance time obtained from the balance test instrument, and the muscle performance parameter is obtained from the muscle movement obtained from the muscle performance test instrument, and
wherein a SPPB result is determined from at least one of parameters including the gait speed parameter, the body balance parameter, and the muscle strength parameter,
wherein the gait speed parameter represents a gait speed in a predetermined interval,
wherein the balance parameter represents a balance maintenance time in predetermined stances, and wherein the muscle performance parameter represents time for sit-to-stand movements in a predetermined count.

13. A non-transitory storage medium readable by a computing system configured to record a program for implementing the diagnosis method of claim 7.

14. A non-transitory storage medium readable by a computing system configured to record a program for implementing the diagnosis method of claim 9.

15. A non-transitory storage medium readable by a computing system configured to record a program for implementing the diagnosis method of claim 12.

* * * * *